United States Patent
Venet et al.

[11] Patent Number: 5,922,734
[45] Date of Patent: Jul. 13, 1999

[54] 6-[TRIAZOLYL[3-(TRIFLUOROMETHYL) PHENYL]METHYL]-2-QUINOLINES AND -QUINOLINETHIONES

[75] Inventors: Marc Gaston Venet, Le Mesnil Esnard; Dominique Jean-Pierre Mabire, La Saussaye; Gerard Charles Sanz, Le Mesnil Esnard, all of France

[73] Assignee: Janssen Pharmaceutica, N.V., Beerse, Belgium

[21] Appl. No.: 08/860,239

[22] PCT Filed: Dec. 21, 1995

[86] PCT No.: PCT/EP95/05173

§ 371 Date: Jun. 16, 1997

§ 102(e) Date: Jun. 16, 1997

[87] PCT Pub. No.: WO96/20200

PCT Pub. Date: Jul. 4, 1996

[30] Foreign Application Priority Data

Dec. 28, 1994 [EP] European Pat. Off. ............ 94.203.773

[51] Int. Cl.[6] .................... A61K 31/47; C07D 401/06
[52] U.S. Cl. ............................. 514/312; 546/157
[58] Field of Search ............... 546/157; 514/312

[56] References Cited

U.S. PATENT DOCUMENTS

| | | | |
|---|---|---|---|
| 4,792,561 | 12/1988 | Walker et al. | 514/312 |
| 4,859,684 | 8/1989 | Raeymaekers et al. | 514/314 |
| 5,028,606 | 7/1991 | Venet et al. | 514/249 |
| 5,157,046 | 10/1992 | Van Wauwe et al. | 514/397 |
| 5,185,346 | 2/1993 | Sang et al. | 514/312 |

OTHER PUBLICATIONS

Cram and Hammand, "Organic Chemistry", McGrawHill Book Co., NY (1964) 2nd Ed., pp. 565–567, 1964.
Chemical Abstracts vol. 81 (19) No. 120419n (1974).
Chemical Abstracts vol. 87 (21) No. 167846p (1977) Hayashi et al.

*Primary Examiner*—Patricia L. Morris
*Attorney, Agent, or Firm*—Mary A. Appollina

[57] ABSTRACT

This invention is concerned with the compounds of formula

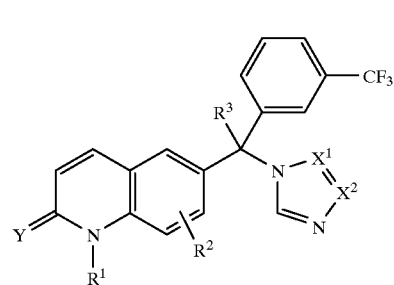

the pharmaceutically acceptable acid addition salts and the stereochemically isomeric forms thereof, wherein: $R^1$ is hydrogen, amino or $C_{1-4}$alkyl; $R^2$ is hydrogen, halo or $C_{1-4}$alkyl; $R^3$ is hydrogen, halo or $C_{1-4}$alkyl; Y is O or S, and —$X^1$=$X^2$— is a bivalent radical having the formula —N=CH—(a-1) or —CH=N—(a-2);

compositions containing the same, and processes of preparing these compounds. It further relates to their use as a medicine, in particular their use as a medicine to treat keratinization disorders.

16 Claims, No Drawings

6-[TRIAZOLYL[3-(TRIFLUOROMETHYL) PHENYL]METHYL]-2-QUINOLINES AND -QUINOLINETHIONES

CROSS-REFERENCE TO RELATED APPLICATION

This application is the national stage of application No. PCT/EP 95/05173, filed on Dec. 21, 1995, which application claims priority from EP 94.203.773.0, filed on Dec. 28, 1994.

The present invention concerns quinolinones and quinolinethiones, compositions containing the same, and processes of preparing these compounds. It further relates to their use as a medicine, in particular, their use as a medicine to treat keratinization disorders.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex. A select group of (1H-triazol-1-ylmethyl) substituted quinolinone and quinolinethiones derivatives invariably being substituted with a 3-(trifluoromethyl)phenyl moiety, is the subject of the present invention. The unexpected superiority of said select group of compounds over the closest art-known compounds lies in their improved ability to suppress keratinization effects.

Hence, the present invention is concerned with compounds of formula

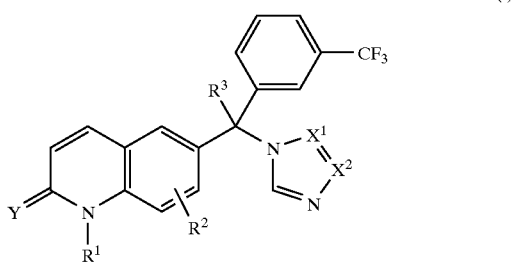

(I)

the pharmaceutically acceptable acid addition salts and the stereochemically isomeric forms thereof, wherein:

$R^1$ is hydrogen, amino or $C_{1-4}$alkyl;
$R^2$ is hydrogen, halo or $C_{1-4}$alkyl;
$R^3$ is hydrogen, halo or $C_{1-4}$alkyl;
Y is O or S; and
—$X^1$=$X^2$— is a bivalent radical having the formula
—N=CH— (a-1) or
—CH=N— (a-2).

As used in the foregoing definitions the term halo is generic to fluoro, chloro, bromo and iodo. The term $C_{1-4}$alkyl defines straight and branched saturated hydrocarbons, having from 1 to 4 carbon atoms such as, for example, methyl, ethyl, propyl, butyl, 1-methylethyl, 1,1-dimethylethyl, 2-methylpropyl and the like.

The pharmaceutically acceptable acid addition salts as mentioned hereinabove are meant to comprise the acid addition salt forms which can conveniently be obtained by treating the base form of the compounds of formula (I) with appropriate acids such as inorganic acids, for example, hydrohalic acid, e.g. hydrochloric or hydrobromic, sulfuric, nitric phosphoric and the like acids; or organic acids, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely, said acid addition salt forms can be converted in the free base forms by treatment with an appropriate base.

The term acid addition salt also comprises the hydrates and the solvent addition forms which the compounds of formula (I) are able to form. Examples of such forms are e.g. hydrates, alcoholates and the like.

The term stereochemically isomeric forms as used herein defines all the possible isomeric forms in which the compounds of formula (I) may occur. Unless otherwise mentioned or indicated, the chemical designation of compounds denotes the mixture of all possible stereochemically isomeric forms, said mixtures containing all diastereomers and enantiomers of the basic molecular structure. In particular, the compounds of formula (I) and some of the intermediates hereinafter have at least one stereogenic center in their structure. This stereogenic center may be present in a R and a S configuration, said R and S notation is used in correspondance with the rules described in Pure Appl. Chem., 1976, 45, 11–30.

Some of the compounds of formula (I) may also exist in their tautomeric forms. Such forms although not explicitly indicated in the above formula are intended to be included within the scope of the present invention. For instance, the compounds of formula (I) wherein $R^1$ is hydrogen may exist in their tautomeric form.

Whenever used hereinafter, the term compounds of formula (I) is meant to include also the pharmaceutically acceptable acid addition salts and all stereoisomeric forms.

Particular compounds of the present invention are those compounds of formula (I) wherein —$X^1$=$X^2$— is a bivalent radical of formula (a-1).

Other particular compounds are those compounds of formula (I) wherein $R^2$ is substituted on the 5 or 8 position of the quinolinone- or quinolinethione moiety.

Of special interest are those compounds wherein —$X^1$=$X^2$— is a bivalent radical of formula (a-1) and Y is O.

Also of special interest are those compounds wherein Y is S and $R^2$ is hydrogen.

Further interesting compounds are those compounds of formula (I) wherein $R^1$, $R^2$ and $R^3$ are hydrogen.

Another group of interesting compounds are those compounds of formula (I) for which the free base form has the R configuration.

Preferred compounds are those compounds of formula (I) wherein —$X^1$=$X^2$— is a bivalent radical of formula (a-1), $R^1$ is hydrogen, amino or methyl, $R^2$ is hydrogen and $R^3$ is hydrogen, halo, methyl or ethyl.

More preferred compounds are those preferred compounds wherein Y is O, $R^1$ is hydrogen or methyl and $R^3$ is hydrogen, methyl or ethyl.

Still more preferred compounds are: 6-[1H- 1,2,4-triazol-1-yl[3-(trifluoromethyl)phenyl]methyl]-2(1H)-quinolinone, the pharmaceutically acceptable acid addition salts and the stereochemically isomeric forms thereof.

Most preferred is the compound (–)-(R)-6-[1H-1,2,4-triazol-1-yl[3-(trifluoromethyl)phenyl]-methyl]-2-(1H)-quinolinone and the pharmaceutically acceptable acid addition salts thereof.

The compounds of formula (I) wherein Y is O, said compounds being represented by formula (I-b), can be prepared in accordance with the procedures described in EP-0,371,564.

The compounds of formula (I-b) may further be converted into compounds of formula (I) wherein Y is S, said compounds being represented by formula (I-c), using art-known transformation reagents such as, for example, phosphorous pentasulfide.

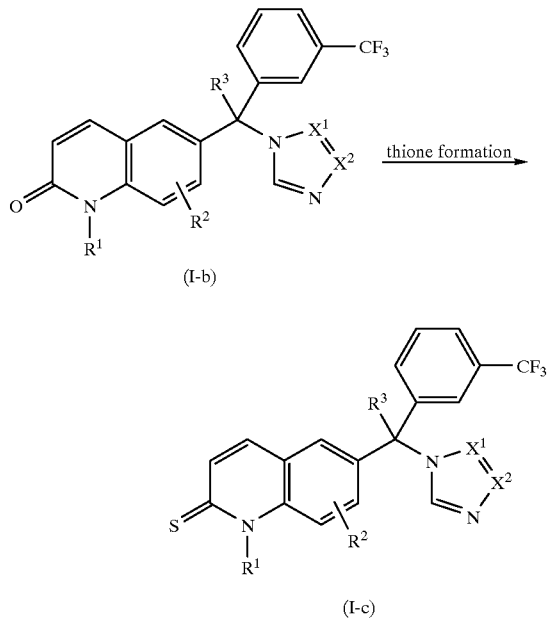

Said compounds of formula (I-c) may be prepared by mixing the reagents in a reaction-inert solvent such as, for example, pyridine. The reaction may suitably be carried out at the reflux temperature of the reaction mixture.

In this and the following preparations, the reaction products may be isolated from the reaction medium and, if necessary, further purified according to methodologies generally known in the art such as, for example, extraction, crystallization, trituration and chromatography.

The compounds of formula (I-b) wherein $R^1$ is hydrogen, said compounds being represented by formula (I-b-1), can be prepared by reacting a nitrone of formula (II) with a suitable ester forming reagent such as, for example, the anhydride of a carboxylic acid, for instance, acetic anhydride, thus forming the corresponding ester on the 2 position of the quinoline moiety. Said quinoline ester can be hydrolyzed in situ to the corresponding quinolinone using a base such as, for example, potassium carbonate. Stirring and elevated temperatures may enhance the rate of the reaction.

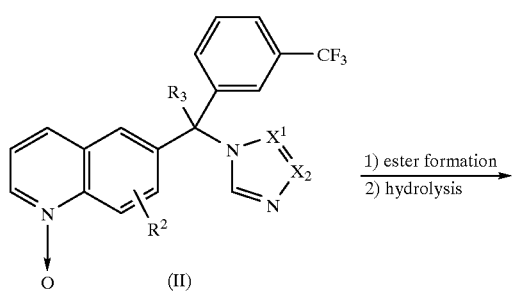

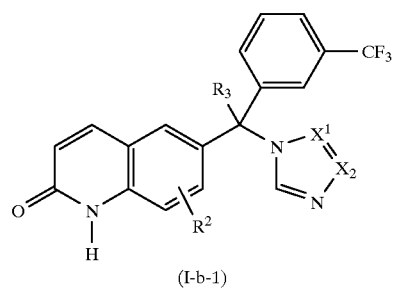

Alternatively, compounds of formula (I-b-1) can be prepared by reacting a nitrone of formula (II) with a sulfonyl containing electrophilic reagent such as, for example, p-toluenesulfonylchloride in the presence of a base such as, for example, aqueous potassium carbonate. The reaction initially involves the formation of a 2-hydroxyquinoline derivative which is subsequently tautomerized to the desired quinolinone derivative. Said reaction may suitably be conducted at room temperature in a reaction-inert solvent such as, for example, dichloromethane or toluene. Stirring and the application of art-known conditions of phase transfer catalysis may enhance the rate of the reaction.

Compounds of formula (I-b-1) may also be prepared by an intramolecular photochemical rearrangement of compounds of formula (II). Said rearrangement can be carried out by dissolving the reagents in a reaction-inert solvent and irradiating at a wavelength of, for instance, 366 nm. It is advantageous to use degassed solutions and to conduct the reaction under an inert atmosphere such as, for example, oxygen free argon or nitrogen gas, in order to minimize undesired side reactions or reduction of quantum yield.

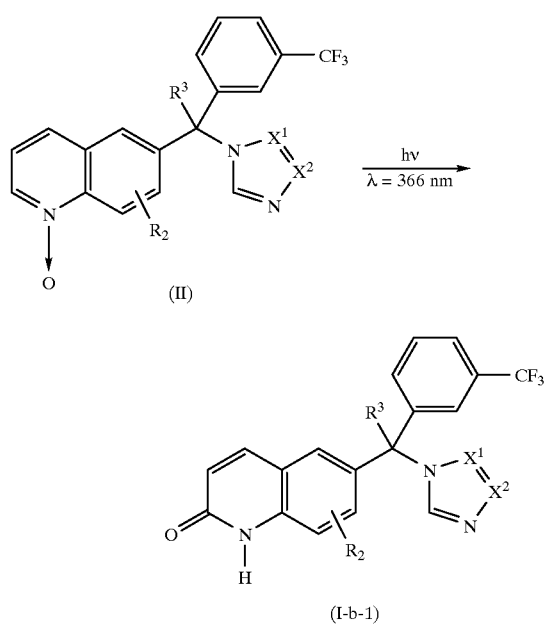

Compounds of formula (I-b-1) may also be converted into compounds of formula (I-b) wherein $R^1$ is $C_{1-4}$alkyl, said compounds being represented by formula (I-b-2). For example, compounds of formula (I-b-1) may be N-alkylated with $C_{1-4}$alkyl-L wherein L is a reactive leaving group such as for example, halo or a sulfonyloxy group, in the presence of a base such as, for example, sodium hydride.

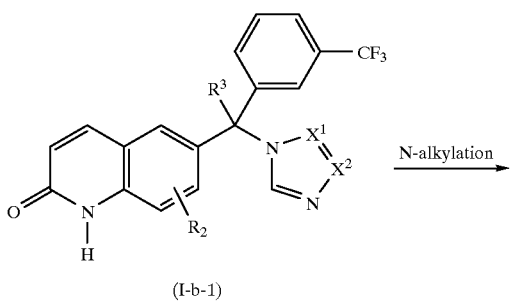

(I-b-1)

↓ N-alkylation

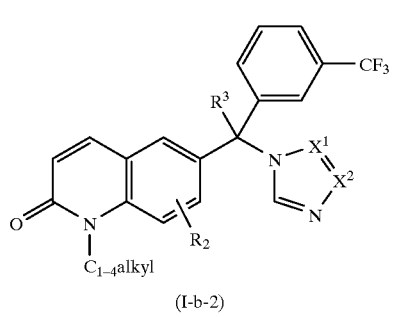

(I-b-2)

Said N-alkylation may conveniently be carried out by mixing the reagents in a reaction-inert solvent such as, for example, N,N-dimethylformamide. It may be advantageous to conduct said N-alkylation under an inert atmosphere such as, for example, argon or nitrogen gas.

The compounds of formula (I-b-1) may also be converted into compounds of formula (I-b) wherein $R^1$ is amino, said compounds being represented by formula (I-b-3). For example, compounds of formula (I-b-3) can be prepared by N-aminating compounds of formula (I-b-1) with an amination agent such as, for example, hydroxylamine-O-sulfonic acid at room temperature in a solvent such as, for example, water and in the presence of a base such as, for example, sodium hydroxide.

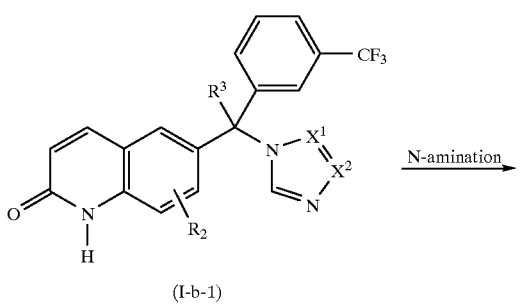

(I-b-1)

↓ N-amination

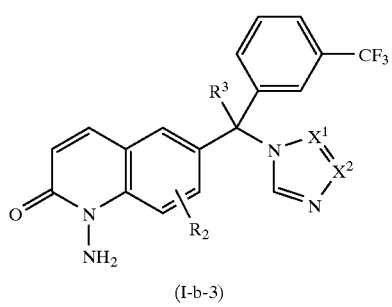

(I-b-3)

Nitrones of formula (II) may be prepared by N-oxidizing quinolines of formula (III) with an appropriate oxidizing agent such as, for example, m-chloro-peroxybenzoic acid or phtalic anhydride in combination with hydrogen peroxide. Said N-oxidation may be carried out by mixing the reagents at room temperature in a reaction-inert solvent such as, for example, dichloromethane. Subsequent to the preparation of the intermediates of formula (II), the compounds of formula (I-b) may conveniently be prepared by way of an in situ reaction.

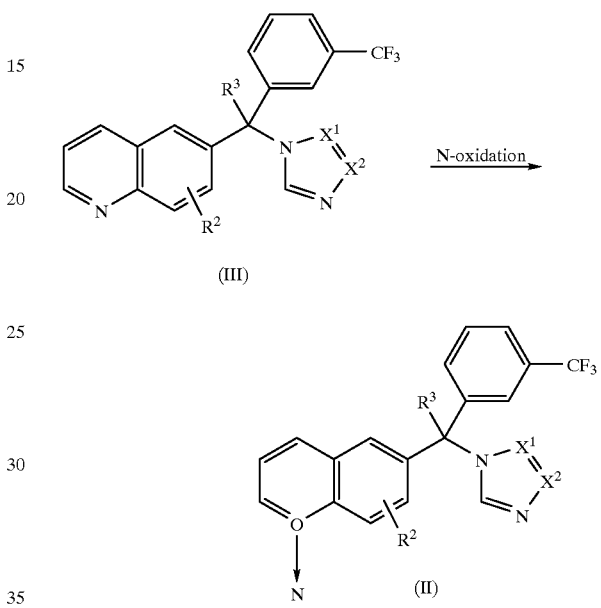

Intermediates of formula (III) can be prepared following the procedures described in EP-0,371,564.

A novel approach to prepare the compounds of formula (I-b-1) wherein $R^3$ is hydrogen, said compounds being represented by formula (I-b-1-a), involves the procedure disclosed in scheme 1. The first step involves the protection of a quinolinone of formula (IV-1) wherein halo represents a halogen atom, in particular, a bromine atom, thus forming a quinoline derivative of formula (IV-2) wherein Z is a protecting group such as, for example, methyl. Said quinoline derivative is reacted with an organolithium compound such as, for example, n-buthyllithium, in a reaction-inert solvent such as, for example, tetrahydrofuran, thus substituting the halogen atom in the 6 position of the quinoline moiety in intermediates of formula (IV-2) with a lithium atom. Said lithiated quinoline intermediate is reacted in situ with 3-trifluorobenzaldehyde or a functional derivative thereof, thus forming an intermediate of formula (IV-3). The formation of intermediates of formula (IV-3) from intermediates of formula (IV-2) may conveniently be carried at low temperatures, preferably at −78° C. Intermediates of formula (IV-3) may be oxidized to the corresponding ketones of formula (IV-4) using art-known oxidizing agents. Said ketones may subsequently be deprotected, thus forming the tautomeric quinolinone derivative of formula (IV-5) in the presence of an acid. Elevated temperatures and stirring may enhance the rate of the transformation reaction.

SCHEME 1

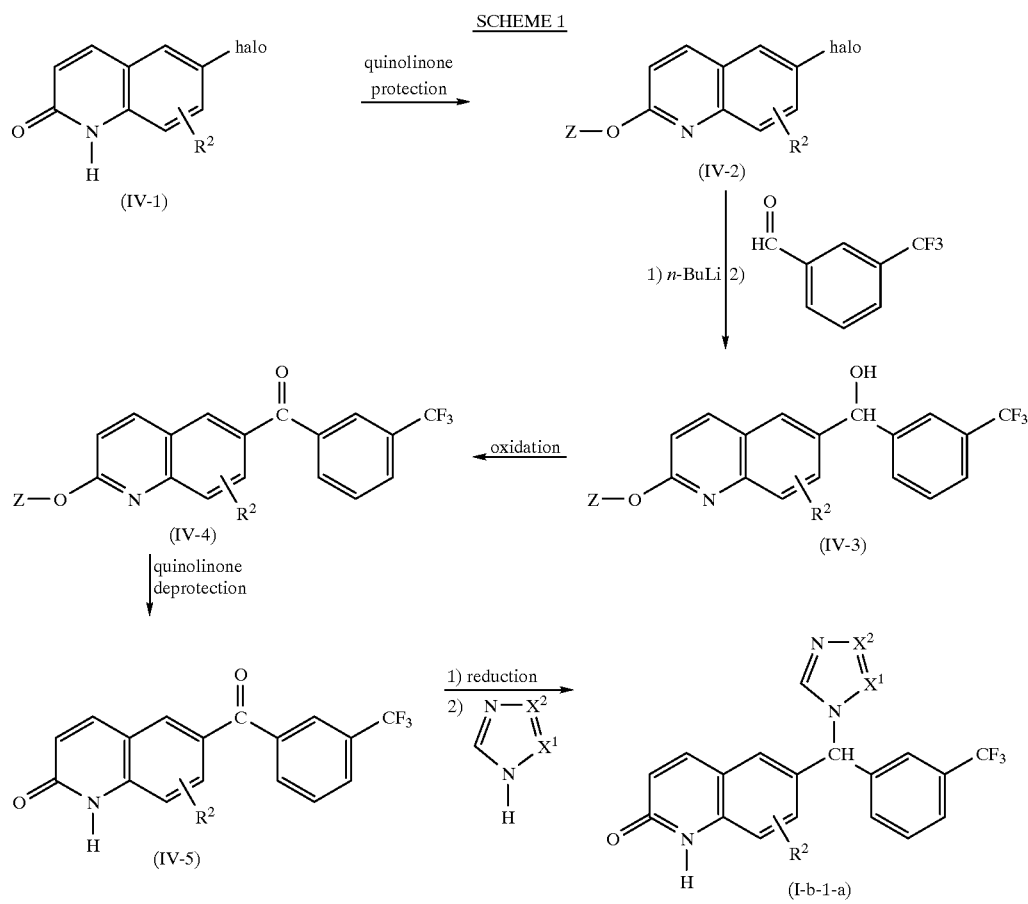

Compounds of formula (I-b-1-a) may be prepared by reductive alkylation of 1,2,4-triazole or 1,3,4-triazole with the compounds of formula (IV-5). Said reaction can conveniently be conducted by stirring and heating the reagents in the presence of formic acid or formamides as reducing agents optionally in the presence of an acid catalyst such as, for example, hydrochloric acid. If desired, the compounds of formula (I-b-1-a) may be further reacted according to the processes described hereinabove for the compounds of formula (I-b) and (I-c).

The compounds of formula (I) and its intermediate compounds as prepared in the hereinabove described processes are generally racemic mixtures of enantiomers which can be separated from one another following art-known resolution procedures. The racemic compounds of formula (I) or its intermediate compounds may be converted into the corresponding diastereomeric salt forms by reaction with a suitable chiral acid such as, for example, camphorsulfonic acid. Said diastereomeric salt forms are subsequently separated, for example, by selective or fractional crystallization and the enantiomers are liberated therefrom by alkali. An alternative manner of separating the enantiomeric forms of the compounds of formula (I) or its intermediate compounds involves liquid chromatography using a chiral stationary phase. Said pure stereochemically isomeric forms may also be derived from the corresponding pure stereochemically isomeric forms of the appropriate starting materials, provided that the reaction occurs stereospecifically. For example, enantiomerically pure forms of the compounds of formula (I) may be prepared from enantiomerically pure forms of compounds of formula (III). The enantiomerically pure compounds of formula (III) may be prepared using art-known separation techniques.

The compounds of the present invention have superior pharmacological properties compared to those of the closest art-compounds in that they are more effective in suppressing keratinization effects which may be demonstrated in the "Vaginal Keratinization Test on Ovariectomized Rats" as is described hereinafter. In view of their ability to suppress keratinization effects, the compounds of formula (I) are useful in the treatment and/or prevention of keratinization disorders such as, for example, acne, psoriasis, severe psoriasis, lamellar ichthyosis, plantar warts, callosities, acanthosis nigricans, lichen planus, molluscum, melasma, corneal epithelial abrasion, geographic tongue, Fox-Fordyce disease, cutaneous metastatic melanoma and keloids, epidermolytic hyperkeratosis, Darier's disease, pityriasis rubra pilaris, congenital ichthyosiform erythroderma, hyperkeratosis palmaris et plantaris, and similar disorders.

The compounds of formula (I) also suppress the plasma elimination of retinoids, such as all-trans-retinoic acid, 13-cis retinoic acid and their derivatives resulting in more sustained tissue concentrations of retinoic acid and improved control of the differentiation and growth of various cell types. The property to delay the metabolism of retinoic acid can be evidenced in various in vitro and in vivo experiments. A particular in vitro procedure is described hereinafter and tests the inhibitory activity of the compounds of formula (I) on the metabolism of retinoic acid in human breast cancer cells. In view of their capability to delay the metabolism of retinoic acid, the present compounds are useful in the prevention and/or the treatment of disorders characterized by abnormal cell proliferation and/or differentiation, such as cancer, and, in particular, keratinization disorders such as those mentioned hereinabove (Van Wauwe et al. J. Pharmacol. Exp. Ther., 1992, 261(2), 773–779).

Further, the compounds of formula (I) are useful in suppressing the metabolism of exogenously administered and of endogenously formed 1α,25-dihydroxy-vitamin $D_3$ (calcitriol). The inhibitory activity of the compounds of formula (I) on the metabolic degradation of calcitriol may be evidenced by measuring the impact of said compounds on the calcitriol degradation in human foreskin keratinocytes, pig kidney cells and human hepatoma cells. In view of their inhibitory effect on the calcitriol metabolism, the compounds of formula (I) can be used in the treatment of vitamin D deficiency states. The "classic" application of vitamin D compounds lies in the field of metabolic bone disorders. Calcitriol has also been described to influence the effects and/or production of interleukins. Further, calcitriol is of use in the treatment of diseases characterized by abnormal cell proliferation and/or differentiation, in particular, keratinization disorders such as those described hereinabove (Bouillon et al., Endocrine Reviews, 1995, 16, 200–257).

In addition, the compounds of formula (I) inhibit the formation of androgens from progestines and inhibit the action of the aromatase enzyme complex which catalyses the formation of estrogens from androgenic steroids in mammals.

In view of the above described uses of the compounds of formula (I), it follows that the present invention provides a method of treating warm-blooded animals suffering from diseases which are characterized by an increased proliferation and/or abnormal differentiation of normal, preneoplastic or neoplastic cells, whether they are epithelial or mesenchymal; whether they are of ectodermal, endodermal or mesodermal origin; or whether they are estrogen dependent, ancrogen dependent or non-estrogen and non-androgen dependent. Said method comprises the systemic or topical administration of a therapeutic amount of a compound of formula (I) effective in treating the above described disorders, in particular keratinization disorders, optionally in the presence of an effective amount of a retinoic acid, a derivative or a stereochemically isomeric form thereof. The present invention further concerns a method of treating patients suffering from a pathological condition which may be beneficially influenced by the administration of calcitriol or a prodrug thereof, in particular keratinization disorders, said method consisting of administering to a patient (a) an effective amount of calcitriol or a prodrug thereof and (b) an effective amount of a compound of formula (I).

Thus, the present invention also relates to compounds of formula (I) as defined hereinabove for use as a medicine, in particular, for use as a medicine to treat keratinization disorders. The present invention further relates to compounds of formula (I) as defined hereinabove in combination with a retinoic acid, a derivative or a stereochemically isomeric form thereof, or in combination with calcitriol or a prodrug thereof, for use as a medicine. The present invention also relates to the use of the compounds of formula (I) in the manufacture of a medicament for the treatment of the above described disorders, in particular, keratinization disorders.

For ease of administration, the subject compounds may be formulated into various pharmaceutical forms. As appropriate compositions there may be cited all compositions usually employed for systemically or topically administering drugs.

To prepare the pharmaceutical compositions of this invention, a therapeutically effective amount of the particular compound, optionally in acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, as a spot-on or as an ointment. Acid addition salts of compounds of formula (I) due to their increased water solubility over the corresponding base form, are obviously more suitable in the preparation of aqueous compositions. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellent such as nitrogen, carbon dioxide, a freon, or without a propellent such as a pump spray, drops, lotions, or a semisolid such as a thickened composition which can be applied by a swab. In particular compositions, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (included scored or coated tablets), capsules, pills, powder packets, wafers, injectable solutions or suspensions, teaspoonfuls, tablespoonfuls and the like, and segregated multiples thereof.

Other such compositons are preparations of the cosmetic type, such as toilet waters, packs, lotions, skin milks or milky lotions. Said preparations contain, besides the active ingredient, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflamatory agents, antibacterials, antifungals, disinfectants, vitamins, sunscreens, antibiotics, or other antiacne agents.

In a further aspect of the invention there are provided particular pharmaceutical or cosmetical compositions which comprise an inert carrier, an effective amount of a compound of formula (I) and an effective amount of a retinoic acid, a derivative thereof or a stereochemically isomeric form thereof. Said retinoic acid containing compositions are particularly useful for treating acne or for retarding the effects of aging of the skin and generally improve the quality of the skin, particularly human facial skin.

Further, the invention also relates to particular pharmaceutical or cosmetical compositions which comprise an inert carrier, an effective amount of a compound of formula (I) and an effective amount of calcitriol or a prodrug thereof. The latter compositions are particularly useful in treating keratinization disorders.

A particular embodiment of the invention relates to a product containing retinoic acid or a derivative thereof and a compound of formula (I) as a combined preparation for simultaneous, separate or sequential use in dermatological disorders. The invention also relates to a product containing calcitriol or a prodrug thereof and a compound of formula (I) as a combined preparation for simultaneous, separate or sequential use in disorders beneficially affected by calcitriol. Such products may comprise, for example, a kit comprising a container with a suitable composition containing a compound of formula (I) and another container with a composition containing calcitriol or a retinoid Such a product may have the advantage that a physician can select on the basis of the diagnosis of the patient to be treated the appropriate amounts of each component and the sequence and timing of the administration thereof.

Those of skill in the treatment of keratinization disorders could determine the effective therapeutic daily amount from the test results presented hereinafter. An effective therapeutic daily amount would be from about 0.1 mg/kg to about 40 mg/kg body weight, more preferably from about 0.3 mg/kg to about 10 mg/kg body weight. It may be appropriate to administer the therapeutically effective dose once daily or as two, three, four or more sub-doses at appropriate intervals throughout the day. Said sub-doses may be formulated as unit dosage forms, for example, containing 0.1 mg to 500 mg, and in particular, 0.5 mg to 50 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereinabove are therefore only guidelines.

The following examples are intended to illustrate and not to limit the scope of the present invention.

EXPERIMENTAL PART

A. Preparation of the Intermediates

EXAMPLE 1 a) A mixture of ethyl 4-amino-2-chlorobenzoate (20 g), glycerol (32.17 g) and sodium 3-nitrobenzenesulfonate (46.73 g) in sulfuric acid (75%) (160 ml) was stirred for 3 hours at 100° C. and for 1 hour at 140° C. After the mixture was cooled to 60° C. and ethanol (200 ml) was added, the mixture was stirred for 16 hours at 60° C. Ethanol was evaporated and the residue was poured into ice water, neutralized with $NH_4OH$ and extracted with ethylacetate. The separated organic layer was dried over $MgSO_4$, filtered and the filtrate evaporated. The residue was purified by column chromatography over silica gel (eluent: $CH_2Cl_2$/ethylacetate 97.5/2.5). The desired pure fractions were collected and evaporated, yielding 7.56 g (28%) ethyl 5-chloro-6-quinolinecarboxylate (intermediate 1).

b) Lithiumaluminiumhydride (1.66 g) was added portionwise to a solution of intermediate 1 (10.11 g) in tetrahydrofuran (325 ml) at 0° C. under $N_2$ and the mixture was stirred for 1 hour. Ethylacetate (70 ml) and water (3 ml) were added to the mixture which was subsequently filtered. The filtrate was dried over $MgSO_4$, filtered and evaporated, yielding 7.9 g (93%) 5-chloro-6-quinolinemethanol (intermediate 2).

c) A mixture of intermediate 2 (7.9 g) and manganese dioxide (10.64 g) in $CH_2Cl_2$ (165 ml) was stirred for 6 hours at room temperature. The mixture was filtered over celite and the filtrate was stirred again with manganese dioxide (10.64 g) for 24 hours. The mixture was filtered over celite and the filtrate evaporated, yielding 7.82 g (100%) 5-chloro-6-quinolinecaeboxaldehyde (intermediate 3). In a similar manner, 8-fluoro-6-quinolinecarboxaldehyde (intermediate 4) was prepared.

EXAMPLE 2 a) A solution of 1-bromo-3-(trifluoromethyl)benzene (10.67 g) in tetrahydrofuran (15 ml) was added dropwise to a suspension of magnesium turnings (1.15 g) in tetrahydrofuran (15 ml). The mixture was cooled to 0° C. and a solution of intermediate 3 (7.57 g) in tetrahydrofuran (90 ml) was added dropwise. The mixture was partitioned between ethylacetate and a saturated aqueous $NH_4Cl$ solution. The organic layer was separated, dried over $MgSO_4$, filtered and the filtrate evaporated. The residue was purified by column chromatography over silica gel (eluent: $CH_2Cl_2/CH_3OH$ 98/2). The pure fractions were collected and evaporated, yielding 10.9 g (81%) (±)-5-chloro-α-[3-(trifluoromethyl)phenyl]-6-quinolinemethanol (intermediate 5).

b) Thionyl chloride (8 ml) was added dropwise to a solution of intermediate 5 (8 g) in $CH_2Cl_2$ (400 ml) at 0° C. and the mixture was stirred at room temperature overnight. The solvent was evaporated and the residue was partitioned between $CH_2Cl_2$ and water which was alkalized with a saturated $K_2CO_3$ solution. The separated organic layer was dried over MgSO4, filtered and the filtrate evaporated, yielding 8.4 g (100%) (±)-5-chloro-6-[chloro[3-(trifluoromethyl) phenyl]methyl]quinoline (intermediate 6).

c) A mixture of intermediate 6 (8.4 g), 1,2,4-triazole (4.89 g) and potassium carbonate (9.78 g) in acetonitrile (300 ml) was stirred and refluxed for 12 hours. The solvent was evaporated and the residue was partitioned between $CH_2Cl_2$ and water. The separated organic layer was dried over $MgSO_4$, filtered and the filtrate evaporated. The residue was purified by column chromatography over silica gel (eluent: $CH_2Cl_2/CH_3OH/NH_4OH$ 98.5/1.5/0.1). The pure fractions were collected and the solvent evaporated. The residue was crystallized from diisopropyl ether/petrol ether, yielding 1.51 g (32%) (±)-5-chloro-6-[1H-1,2,4-triazol-1-yl[3-(trifluoromethyl)phenyl]-methyl]quinoline (intermediate 7; mp. 144.5° C.). In a similar manner, there were prepared: (±)-8-methyl-6-[1H-1,2,4-triazol-1-yl[3-(trifluoromethyl)

phenyl]methyl]quinoline (intermediate 8; mp. 108.9° C.) and (±)-8-fluoro-6-[1H-1,2,4-triazol-1-yl[3-(trifluoromethyl) phenyl]methyl]quinoline (intermediate 9; mp. 146.6° C.).

EXAMPLE 3

The racemic mixture of 6-[1H-1,2,4-triazol-1-yl[3-(trifluoromethyl)phenyl]methyl]-quinoline (10 g), disclosed and exemplified in EP-371,564 was separated into its pure enantiomers on a Chiracell OD® column (eluent: ethanol/hexanes 1/1). The pure fractions of the first eluted peak were collected, combined and the solvent evaporated, yielding 3.6 g (+)-(S)-6-[1H-1,2,4-triazol- 1-yl[3-(trifluoromethyl) phenyl]methyl]-quinoline (intermediate 10). The pure fractions of the second eluted peak were collected, combined and partitioned with diethyl ether. The separated organic layer was filtered and the solvent evaporated, yielding 3.48 g (−)-(R)-6-[1H-1,2,4-triazol-1-yl[3-(trifluoromethyl) phenyl]methyl]-quinoline (intermediate 11).

EXAMPLE 4

Iodomethane (8.8 ml) was added to a stirring mixture of (±)-6-[1H-1,2,4-triazol-1-yl[3-(trifluoromethyl)phenyl] methyl]quinoline (10 g) in N,N-dimethylformamide (100 ml) at 0° C. under $N_2$. Potassium t-butoxide (9.5 g) was added portionwise and the mixture was stirred for 2 hours at room temperature. The mixture was partitioned between ice water and $CH_2Cl_2$. The separated organic layer was washed with water, dried over $MgSO_4$, filtered and the filtrate evaporated. The oily residue was purified by column chromatography over silica gel (eluent: toluene/2-propanol 94/6). The pure fractions were collected and evaporated. The residue was converted into the nitric acid salt (1:2) in $CH_3OH$ and crystallized from 2-propanone/diethyl ether, yielding 1.15 g (9%) (±)-6-[1H-1,2,4-triazol-1-yl[3-(trifluoromethyl)phenyl]ethyl]quinolilne dinitrate (intermediate 12; mp. 116.4° C.). In a similar manner, there were prepared: (±)-6-[1H-1,2,4-triazol-1-yl[3-(trifluoromethyl)phenyl]propyl]quinoline (intermediate 13); (±)-6-[1H-1,2,4-triazol-1-yl[3-(trifluoromethyl)phenyl]2-methylpropyl]quinoline (intermediate 14); and (±)-6-[1H-1, 2,4-triazol-1-yl[3-(trifluoromethyl)phenyl]pentyl]quinoline (intermediate 15).

EXAMPLE 5

Potassium t-butoxide (0.945 g) was added portionwise to a stirring mixture of (±)-6-[1H-1,2,4-triazol-1-yl[3-(trifluoromethyl)phenyl]methyl]quinoline (2.7 g) in N,N-dimethylformamide (80 ml) at 0° C. under $N_2$. The mixture was stirred for 30 minutes at 0 ° C. and N-fluorosultam (2.43 g), disclosed in Helv. Chim. Acta 72 p. 1248 (1989), was added. Subsequently the mixture was stirred at 0° C. for 1 hour and at room temperature for 1 hour. A few ml of water were added and the solvent was evaporated. The residue was partitioned between water and ethylacetate. The separated organic layer was washed with water, dried over $MgSO_4$, filtered and the filtrate evaporated. The oily residue was purified by column chromatography over silica gel (eluent: $CH_2Cl_2/CH_3OH$ 98/2). The pure fractions were collected and evaporated. The residue was converted into the ethanedioic acid salt (1:1) in 2-propanone/diethyl ether, yielding (±)-6-[fluoro(1H-1,2,4-triazol-1-yl)[3-trifluoromethyl)phenyl]methyl]quinoline ethanedioate (intermediate 16; mp. 142.6° C.).

EXAMPLE 6

3-Chloroperoxybenzoic acid (49 g) was added portionwise to a solution of intermediate 11 (50.3 g) in $CH_2Cl_2$ (500 ml) and the mixture was stirred for 1 hour at room temperature. The mixture was partitioned with a 10% $NaHCO_3$ solution. The separated organic layer was washed with a saturated NaCl solution, dried over $MgSO_4$, filtered and the filtrate evaporated, yielding (−)-(R)-6-[1H-1,2,4-triazol-1-yl [3-(trifluoromethyl)-phenyl]methyl]quinoline, 1-oxide (intermediate 17; mp. 123.2° C.). In a similar manner, the following intermediates were prepared.

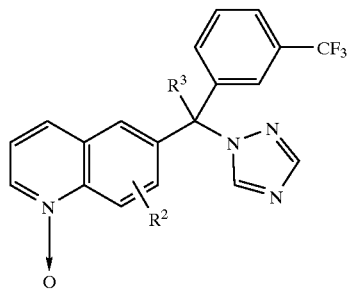

| Intermediate | $R^2$ | $R^3$ | Phys. Prop. (mp. in ° C.) |
|---|---|---|---|
| 17 | H | H | (−)-(R); 123.2 |
| 18 | H | H | (+)-(S); 124.2 |
| 19 | H | H | (±); 206.8 |
| 20 | H | $CH_3$ | (±) |
| 21 | H | F | (±) |
| 22 | H | —$CH_2CH_3$ | (±) |
| 23 | H | —$CH(CH_3)_2$ | (±) |
| 24 | H | —$(CH_2)_3CH_3$ | (±) |
| 25 | 8-$CH_3$ | H | (±) |
| 26 | 5-Cl | H | (±) |
| 27 | 8-F | H | (±) |

EXAMPLE 7 a) Butyllithium (12.5 ml) was added dropwise at −78° C. to a solution of 6-bromo-2-methoxyquinoline (4 g) in tetrahydrofuran (160 ml). After complete addition the mixture was stirred at −78° C. for 15 minutes. A solution of 3-(trifluoromethyl)-benzaldehyde (3.51 g) in tetrahydrofuran (40 ml) was added dropwise and the mixture was stirred at −78° C. for 30 minutes, then quenched with water (50 ml) and extracted with ethylacetate. The organic layer was separated, washed with brine, dried over $MgSO_4$, filtered and the solvent was evaporated. The residue was purified by column chromatography over silica gel (eluent: $CH_2Cl_2/CH_3OH$ 97/3). The pure fractions were collected and the solvent was evaporated, yielding 3.7 g (66%) of (±)-2-methoxy-α-[3-(trifluoromethyl)phenyl]-6- quinoline methanol (intermediate 28).

b) A mixture of intermediate 28 (1 g) and HCl (25 ml; 3 N) was stirred and refluxed for 2 hours. The solution was basified with NaOH and extracted with $CH_2Cl_2$. The organic layer was separated, washed with brine, dried over $MgSO_4$, filtered and the solvent was evaporated, yielding 1.8 g of (±)-6-[hydroxy[3-(trifluoromethyl)phenyl]methyl]-2(1H-quinolinone (intermediate 29).

c) Thionylchloride (12.3 ml) was added dropwise at 0° C. to a solution of intermediate 29 (12.3 g) in $CH_2Cl_2$ (900 ml) and the mixture was stirred for 1 hour. Thionylchloride (12.3 ml) was added again dropwise at 0° C. and the mixture was stirred at room temperature for 1 hour. Thionylchloride (12.3 ml) was added again dropwise at 0° C. and the mixture was stirred at room temperature for 1 hour. The mixture was poured into ice and extracted. The organic layer was dried over MgSO$_4$, filtered off and the solvent was evaporated, yielding 13 g (100%) of (±)-6-[chloro[3-(trifluoromethyl) phenyl]methyl]-2(1H)-quinolinone (intermediate 30).

B. Preparation of the Compounds of Formula (I)

EXAMPLE 8

A 10% K$_2$CO$_3$ solution (700 ml) and p-toluenesulfonyl chloride (36.8 g) were added to a solution of intermediate 17 (52.5 g) in CH$_2$Cl$_2$ (700 ml) and the mixture was stirred at room temperature for 1 hour. The mixture was washed with a saturated NaCl solution and the separated organic layer was dried over MgSO$_4$, filtered and the filtrate evaporated. The residue was purified by column chromatography over silica gel (eluent: CH$_2$Cl$_2$/CH$_3$OH 96.5/3.5). The pure fractions were collected and evaporated. The residue was crystallized from methyl ethyl keton/diisopropyl ether, yielding 15.3 g (29%) (−)-(R)-6-[1H-1,2,4-triazol-1-yl[3-(trifluoromethyl)phenyl]methyl]-2(1H)-quinolinone (compound 1; mp. 192.8° C.; $[\alpha]_D^{20}$=−41.05° (c=99.87 mg/10 ml methanol)).

EXAMPLE 9

Alternatively, compound 1 was prepared by stirring a solution of intermediate 17 (1.2 g) in acetic anhydride (10 ml) for 12 hours at 140° C. Excessive acetic anhydride was evaporated, the mixture was alkalized with a 10% K$_2$CO$_3$ solution and extracted with CH$_2$Cl$_2$. The separated organic layer was washed with a saturated NaCl solution, dried over MgSO$_4$, filtered and the filtrate evaporated. The residue was purified by column chromatography over silica gel (eluent: CH$_2$Cl$_2$/CH$_3$OH 95/5). The pure fractions were collected, evaporated and further purified by column chromatography over Chiracel AD® (eluent: n-hexane/ethanol 90/10). The pure fractions were collected and evaporated, yielding 0.235 g (33.7%) of compound 1 (mp. 176.0° C.; $[\alpha]_D^{20}$=−45.62° (c=10.96 mg/10 ml methanol)). The above reaction procedure was repeated a number of times and a mixture of the resulting fractions was dissolved in methyl ethyl keton (300 ml) and heated to complete dissolution. The mixture was filtered warm. The filtrate was rested for 18 hours, allowing the compound to recrystallize. The precipitate was filtered off, washed with diisopropyl ether (100 ml) and dried, yielding 118 g (90.8%) of compound 1. This fraction was dried again, yielding 109.5 g (64.2%) of compound 1 (mp. 195° C.; $[\alpha]_D^{20}$=−42.12° (c=99.23 mg/10 ml methanol)).

EXAMPLE 10

A mixture of intermediate 30 (0.846 g), 1,2,4-triazole (0.346 g) and potassium carbonate (0.7 g) in CH$_3$CN (30 ml) was stirred and refluxed for 2 hours. The solvent was evaporated and the residue was taken up in water and extracted with CH$_2$Cl$_2$. The organic layer was dried MgSO$_4$, filtered and the solvent was evaporated. The residue was purified by column chromatography over silica gel (eluent: CH$_2$Cl$_2$/CH$_3$OH/NH$_4$OH 98/2/0.1) and the solvent of the desired fraction was evaporated, yielding 0.25 g (27%) of (±)-6-[1H-1,2,4-triazol-1-yl[3-(trifluoromethyl)phenyl] methyl]-2(1H)-quinolinone (compound 3).

The following table lists compounds that were prepared in a similar way as in one of the hereinabove mentioned examples.

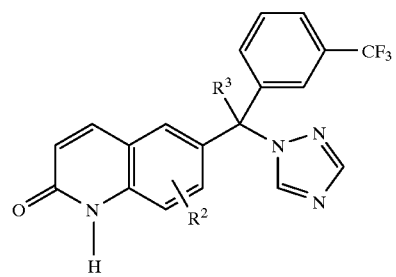

| Comp. No. | Example | R$^2$ | R$^3$ | Phys. Prop. (mp. in ° C.) |
|---|---|---|---|---|
| 1 | 8 | H | H | (−)-(R); 192.8; $[\alpha]_D^{20}$ = −41.05° (c = 99.87 mg/10 ml methanol) |
| 1 | 9 | H | H | (−)-(R); 195; $[\alpha]_D^{20}$ = −42.12° (c = 99.23 mg/10 ml methanol) |
| 2 | 8 | H | H | (+)-(S); 193.9; $[\alpha]_D^{20}$ = 40.72° (c = 98.72 mg/10 ml methanol) |
| 2 | 9 | H | H | (+)-(S); 172.0; $[\alpha]_D^{20}$ = 45.62° (c = 10.96 mg/10 ml methanol) |
| 3 | 9 | H | H | (±); 192.2 |
| 3 | 10 | H | H | (±) |
| 4 | 8 | H | CH$_3$ | (±); 255.6 |
| 5 | 8 | H | F | (±); 231.6 |
| 6 | 8 | H | CH$_2$CH$_3$ | (±); 170.3 |
| 7 | 8 | H | CH(CH$_3$)$_2$ | (±); 205.0 |
| 8 | 8 | H | (CH$_2$)$_3$CH$_3$ | (±); 217.1 |
| 9 | 8 | 8-CH$_3$ | H | (±); 174.9 |
| 10 | 8 | 5-Cl | H | (±); 155.6 |
| 11 | 8 | 8-F | H | (±); 182.6 |

EXAMPLE 11

A mixture of compound 3 (10 g) in N,N-dimethylformamide (100 ml) was stirred at room temperature under N$_2$. Sodium hydride (0.51 g) was added portionwise and the mixture was stirred for 15 minutes. The mixture was cooled, iodomethane was added dropwise and the reaction mixture was stirred for 12 hours. The solvent was evaporated and the residue was partitioned between CH$_2$Cl$_2$ and water. The separated organic layer was dried over MgSO$_4$, filtered and the filtrate evaporated. The oily residue was purified by column chromatography over silica gel (eluent: CH$_2$Cl$_2$/CH$_3$OH/NH$_4$OH 98/2/0.1). The pure fractions were collected and the solvent was evaporated. The residue was crystallized from methyl ethyl keton/diethyl ether, yielding 2.9 g(28%) (±)-1methyl-6-[1H-1,2,4-triazol-1-yl[3-(trifluoromethyl)phenyl]methyl]-2(1H)-quinolinone (compound 12; mp. 186.7° C.). In a similar manner, the following compounds were prepared:

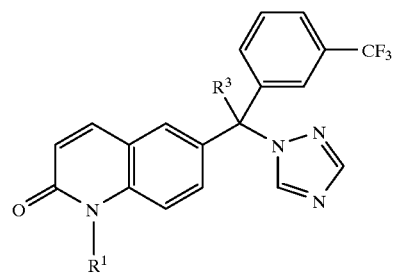

| Comp. No. | R$^1$ | R$^2$ | Physical Properties (mp. in ° C.) |
|---|---|---|---|
| 12 | H | CH$_3$ | (±); 186.7 |
| 13 | F | CH$_3$ | (±); 148.1 |

-continued

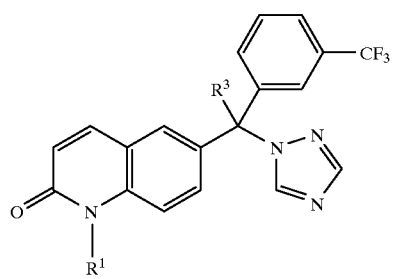

| Comp. No. | R¹ | R² | Physical Properties (mp. in °C.) |
|---|---|---|---|
| 14 | $CH_3$ | $CH_3$ | (±); 159.1 |
| 15 | $CH_2CH_3$ | $CH_3$ | (±); 130.2 |
| 16 | $CH_3$ | $CH_2CH_3$ | (±); 125.8 |
| 17 | $CH_3$ | $(CH_2)_2CH_3$ | (±); 177.4 |
| 18 | $CH_3$ | $(CH_2)_3CH_3$ | (±); 143.5 |
| 19 | $CH_3$ | $CH_2CH(CH_3)_2$ | (±); 189.5 |

EXAMPLE 12

A mixture of compound 3 (7.3 g) and NaOH (4.12 g) in water (20 ml) was stirred at room temperature for 15 minutes. Hydroxylamine-O-sulfonic acid (6.3 g) was added portionwise and the mixture was stirred for 12 hours. The precipitate was filtered off and crystallyzed from 2-propanol, yielding 2.3 g (±)-(1-amino-6-[1H-1,2,4-triazol-1-yl-[3-(trifluoromethyl)phenyl]methyl]-2(1H)-quinolinone (compound 20; mp. 222.3° C.).

EXAMPLE 13

A mixture of compound 12 (7 g) and phosphorus pentasulfide (8.1 g) in pyridine (100 ml) was stirred and refluxed for 4 hours. The solvent was evaporated, the residue was partitioned between water and $CH_2Cl_2$. The separated organic layer was dried over $MgSO_4$, filtered and the filtrate evaporated. The residue was purified by column chromatography over silica gel (eluent: $CH_2Cl_2/CH_3OH/NH_4OH$ 99/1/0.1). The pure fractions were collected and evaporated. The residue was crystallized from diisopropyl ether/methyl ethyl keton/2-propanone, yielding 1.4 g (20%) (±)-1-methyl-6-[1H-1,2,4-triazol-1-yl[3-(trifluoromethyl)phenyl]methyl]-2(1H)-quinolinethione (compound 21; mp. 143.7° C.). In a similar way, (±)-6-[1H-1,2,4-triazol-1-yl[3-(trifluoromethyl]phenyl]methyl]-2-quinolinethiol (compound 22) was prepared.

EXAMPLE 14

Compound 1 (3.7 g) was dissolved in ethanol (50 ml). HBr (gas) was bubbled through the mixture for 2 minutes. The solvent was evaporated and the residue was dissolved in $CH_3CN/C_2H_5OH$ 80/20. The solvent was evaporated and the residue was triturated in methyl isobutyl keton. The precipitate was filtered off and dried. This fraction was recrystallized from 2-propanone/2-propanol (35 ml/15 ml). The precipitate was filtered off and dried. This fraction was recrystallized from ethanol in a closed chamber, saturated with 2-propanone. The liquid was decanted and the crystals were dried, yielding 0.74 g (16.4%) of (R)-6-[1H-1,2,4-triazol-1-yl[3-(trifluoromethyl)phenyl]-methyl]-2(1H)-quinolinone monohydrobromide (1:1) (compound 23; mp. 220° C.).

C. Pharmacological examples

Example 15: Inhibition of retinoic acid (RA) metabolism

MCF-7 human breast cancer cells were grown as stock cultures according to art-known protocols. One day before the experiment, RA is added to the stock cultures to stimulate RA-metabolism. At the start of the experiment, cell suspensions were incubated in a tissue culture medium containing $^3$H-RA as the substrate. Different concentrations of the test compound (dissolved in 1% DMSO) were added to the incubation mixtures, and at the end of the incubation, the unmetabolized RA is separated from its polar metabolites. The fraction containing the polar $^3$H-labelled metabolites was collected and counted in a scintillation counter. For each experiment, a control and a blank incubation were run in parallel. The $IC_{50}$ values listed in table 1 are the concentrations needed to reduce the amount of metabolites to 50% of the control.

Example 16: "Vaginal Keratinization Test on Ovariectomized Rats"

Ovariectomized rats were injected subcutaneously with a sesame oil solution containing 100 μg of estradiol undecylate in a volume of 0.1 ml per 100 g body weight and control animals were injected with sesame oil. On day one, two and three, test animals were treated once daily with a per os dose of the test compound and control animals with the drug vehicle (PEG 200). One day after the last treatment, the animals were sacrificed and their vaginas were processed for histological evaluation according to the method described in J. Pharmacol. Exp. Ther. 261(2), 773–779 (1992). A dose at which 50% of the tested rats show complete suppression of the estradiol undecylate induced keratinization effects is defined as an active dose. The lowest active dose (LAD) for the compounds of the present invention is listed in table 1.

The unexpected superiority of the compounds of the present invention over the closest art-known compounds is demonstrated in table 2. In said table, the keratinization effect of the present compound number 3 is compared to the structurally closest art-known compounds, the latter being disclosed in EP-0,371,564.

TABLE 1

| Compound Number | Keratinization (LAD in mg/kg) | RA Metabolism ($IC_{50}$ in M) |
|---|---|---|
| 1 | 1.25 | $8.5 \times 10^{-7}$ |
| 2 | >40 | $3.85 \times 10^{-6}$ |
| 3 | 2.5 | $8.51 \times 10^{-7}$ |
| 4 | 5 | $5.1 \times 10^{-7}$ |
| 5 | 5 | $>1 \times 10^{-5}$ |
| 6 | 10 | $1.82 \times 10^{-8}$ |
| 7 | >20 | $2.7 \times 10^{-7}$ |
| 9 | 10 | $7.06 \times 10^{-7}$ |
| 10 | 10 | $7.64 \times 10^{-7}$ |
| 11 | 10 | $1.54 \times 10^{-7}$ |
| 12 | 2.5 | $8.59 \times 10^{-6}$ |
| 13 | — | $1.02 \times 10^{-8}$ |
| 14 | 5 | $3.25 \times 10^{-9}$ |
| 15 | 2.5 | $>1 \times 10^{-6}$ |
| 16 | 10 | $>1 \times 10^{-6}$ |
| 17 | >10 | $1.07 \times 10^{-8}$ |
| 18 | >10 | $>1 \times 10^{-7}$ |
| 19 | >10 | $>1 \times 10^{-7}$ |
| 20 | 5 | $1.47 \times 10^{-6}$ |
| 21 | 5 | $4.37 \times 10^{-6}$ |

TABLE 2

| EP-0,371,564 | | present invention | |
|---|---|---|---|
| Compound | LAD (mg/kg) | Compound | LAD (mg/kg) |
| Comp. No. 11-a | 40 | Comp. No. 3 | 2.5 |
| Comp. No. 66-a | 10 | | |

D. Composition examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable acid addition salt thereof.

Example 17: oral solution 9 g of methyl 4-hydroxybenzoate and 1 g of propyl 4-hydroxy-benzoate were dissolved in 4 l of boiling purified water. In 3 l of this solution were dissolved first 10 g of 2,3-dihydroxybutanedioic acid and thereafter 20 g of A.I. 1 and/or 0.2 g of A.I. 2. The latter solution was combined with the remaining part of the former solution and 12 l 1,2,3-propane-triol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of A.I. 1 and/or 0.05 mg of A.I. 2 per teaspoonful (5 ml). The resulting solution was filled in suitable containers.

Example 18: oral drops 500 g of the A.I. was dissolved in 0.5 l of 2-hydroxypropanoic acid and 1.5 l of the polyethylene glycol at 60~80° C. After cooling to 30~40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

Example 19: capsules 20 g of A.I. 1 and/or 0.2 g of A.I. 2, 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelatin capsules, each comprising 20 mg of A.I. 1 and/or 0.2 mg of A.I. 2.

Example 20: injectable solution 0.5 mg A.I. 1 and/or 0.05 mg A.I. 2, 50 mg glucose anhydrous and 0.332 ml concentrated hydrochloric acid were mixed with 0.8 ml water for injections. Sodium hydroxide was added until pH=3.2±0.1 and water was added to 1 ml. The solution was sterilized and filled in sterile containers.

Example 21: film-coated tablets

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90®) in about 200 ml of water. The wet powder mixture was sieved, dried and sieved again. Then there was added 100 g microcrystalline cellulose (Avicel®) and 15 g hydrogenated vegetable oil (Sterotex®). The whole was mixed well and compressed into tablets, giving 10.000 tablets, each comprising 10 mg of the active ingredient.

Coating

To a solution of 10 g methyl cellulose (Methocel 60 HG®) in 75 ml of denaturated ethanol there was added a solution of 5 g of ethyl cellulose (Ethocel 22 cps®) in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension (Opaspray K-1-2109®) and the whole was homogenated. The tablet cores were coated with the thus obtained mixture in a coating apparatus.

Example 22: 2% cream 75 mg stearyl alcohol, 2 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70 to 75° C. while using a homogenizer for liquids. The resulting emulsion is allowed to cool to below 25° C. while continuously mixing. A solution of 20 mg A.I., 1 mg polysorbate 80 and purified water and a solution of 2 mg sodium sulfite anhydrous in purified water are next added to the emulsion while continuously mixing. The cream, 1 g of the A.I. is homogenized and filled into suitable tubes.

Example 23: 2% topical gel

To a solution of 200 mg hydroxypropyl b-cyclodextrine in purified water is added 20 mg of A.I. while stirring. Hydrochloric acid is added until complete dissolution and then sodium hydroxide is added until pH 6.0. This solution is added to a dispersion of 10 mg carrageenan PJ in 50 mg propylene glycol while mixing. While mixing slowly, the mixture is heated to 50° C. and allowed to cool to about 35° C. whereupon 50 mg ethyl alcohol 95% (v/v) is added. The rest of the purified water q.s. ad 1 g is added and the mixture is mixed to homogenous.

Example 24: 2% topical cream

To a solution of 200 mg hydroxypropyl b-cyclodextrine in purified water is added 20 mg of A.I. while stirring. Hydrochloric acid is added until complete dissolution and next sodium hydroxide is added until pH 6.0. While stirring, 50 mg glycerol and 35 mg polysorbate 60 are added and the mixture is heated to 70° C. The resulting mixture is added to a mixture of 100 mg mineral oil, 20 mg stearyl alcohol, 20 mg cetyl alcohol, 20 mg glycerol monostearate and 15 mg sorbate 60 having a temperature of 70° C. while mixing slowly. After cooling down to below 250° C., the rest of the purified water q.s. ad 1 g is added and the mixture is mixed to homogenous.

Example 25: 2% liposome formulation

A mixture of 2 g A.I. microfine, 20 g phosphatidyl choline, 5 g cholesterol and 10 g ethyl alcohol is stirred and heated at 55–60° C. until complete dissolution and is added to a solution of 0.2 g methyl paraben, 0.02 g propyl paraben, 0.15 g disodium edetate and 0.3 g sodium chloride in purified water while homogenizing. 0.15 g Hydroxypropyl-methylcellulose in purified water ad 100 g is added and the mixing is continued until swelling is complete.

Example 26: 2% liposome formulation

A mixture of 10 g phosphatidyl choline and 1 g cholesterol in 7.5 g ethyl alcohol is stirred and heated at 40° C. until complete dissolution. 2 g A.I. microfine is dissolved in purified water by mixing while heating at 40° C. The alcoholic solution is added slowly to the aqueous solution while homogenizing during 10 minutes. 1.5 g Hydroxypropyl-methylcellulose in purified water is added while mixing until swelling is complete. The resulting solution is adjusted to pH 5.0 with sodium hydroxide 1 N and diluted with the rest of the purified water ad 100 g.

We claim:

1. A compound of formula

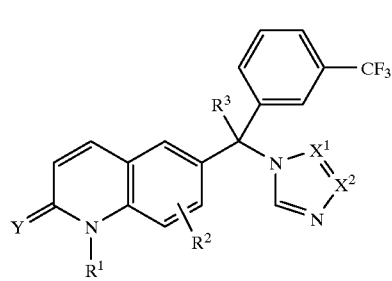

a pharmaceutically acceptable acid addition salt or a stereochemically isomeric form thereof, wherein:
$R^1$ is hydrogen, amino or $C_{1-4}$alkyl;
$R^2$ is hydrogen, halo or $C_{1-4}$alkyl;
$R^3$ is hydrogen, halo or $C_{1-4}$alkyl;
Y is O or S; and
—$X^1$=$X^2$— is a bivalent radical having the formula
—N=CH— (a-1) or
—CH=N— (a-2).

2. A compound according to claim 1 wherein —$X^1$=$X^2$— is a bivalent radical of formula (a-1).

3. A compound according to claim 2, wherein Y is O.

4. A compound according to claim 3, wherein $R^1$ is hydrogen or methyl, $R^2$ is hydrogen and $R^3$ is hydrogen, methyl or ethyl.

5. A compound according to claim 1, wherein the compound is (−)-(R)-6-[1H-1,2,4-triazol-1-yl[3-(trifluoromethyl]phenyl]methyl]-2(1H)-quinolinone; or the pharmaceutically acceptable acid addition salts thereof.

6. A composition comprising a pharmaceutically acceptable carrier and, as active ingredient, a therapeutically effective amount of a compound as claimed in claim 1.

7. A composition comprising a pharmaceutically acceptable carrier and, as active ingredient, a therapeutically effective amount of a compound as claimed in claim 2.

8. A composition comprising a pharmaceutically acceptable carrier and, as active ingredient, a therapeutically effective amount of a compound as claimed in claim 3.

9. A composition comprising a pharmaceutically acceptable carrier and, as active ingredient, a therapeutically effective amount of a compound as claimed in claim 4.

10. A composition comprising a pharmaceutically acceptable carrier and, as active ingredient, a therapeutically effective amount of a compound as claimed in claim 5.

11. A method of treating psoriasis in patients in need of the same which comprises the topical or systemic administration to said patients of a therapeutically effective amount of a compound as claimed in claim 1.

12. A method of treating psoriasis in patients in need of the same which comprises the topical or systemic administration to said patients of a therapeutically effective amount of a compound as claimed in claim 2.

13. A method of treating psoriasis in patients in need of the same which comprises the topical or systemic administration to said patients of a therapeutically effective amount of a compound as claimed in claim 3.

14. A method of treating psoriasis in patients in need of the same which comprises the topical or systemic administration to said patients of a therapeutically effective amount of a compound as claimed in claim 4.

15. A method of treating psoriasis in patients in need of the same which comprises the topical or systemic administration to said patients of a therapeutically effective amount of a compound as claimed in claim 5.

16. A process of preparing a compound as claimed in claim 1, characterized in that: a) a nitrone of formula

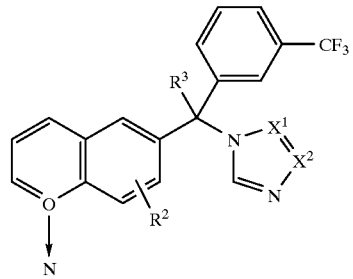

(II)

wherein $R^2$, $R^3$ and $-X^1=X^2-$ are defined as in claim 1, is reacted with p-toluenesulfonylchloride thus obtaining a compound of formula

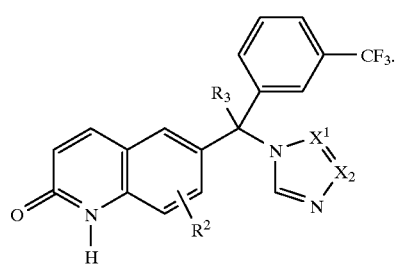

(I-b-1)

* * * * *